United States Patent [19]

Fair

[11] Patent Number: 4,533,355
[45] Date of Patent: Aug. 6, 1985

[54] LOOSE-FITTING OSTOMY GARMENT

[76] Inventor: Marjorie A. Fair, 7707 W. Villa Theresa Dr., Peoria, Ariz. 85345

[21] Appl. No.: 606,532

[22] Filed: May 3, 1984

[51] Int. Cl.³ .............................. A61F 5/40; A41B 9/02
[52] U.S. Cl. .................................... 604/345; 2/400;
   2/402; 2/403; 2/406; 2/238; 604/343; 604/344
[58] Field of Search ................ 604/345, 343, 344;
   2/400, 402, 403, 406, 238

[56] References Cited

U.S. PATENT DOCUMENTS

| | | | |
|---|---|---|---|
| 2,688,327 | 9/1954 | Berg | 128/283 |
| 2,691,375 | 10/1954 | Tasse | 604/345 |
| 2,778,362 | 1/1957 | Pollock et al. | 604/345 |
| 3,421,505 | 1/1969 | Freeman et al. | 604/345 |
| 3,468,310 | 9/1969 | Kimball | 604/345 |
| 4,145,763 | 3/1979 | Abrams et al. | 2/403 |
| 4,173,976 | 11/1979 | Bloomquist et al. | 128/159 |

Primary Examiner—Arthur P. Demers
Attorney, Agent, or Firm—Nelson & Roediger

[57] ABSTRACT

A loose-fitting garment for individuals wearing an ostomy appliance with an encircling band which contacts the body above the stoma. The downwardly extending fabric which covers the torso has a large vertical opening therein and a pocket on the exterior covering a portion of the opening. The appliance fitted to the stoma extends through the opening and rests in the pocket. A cover flap is provided to shield the appliance from view.

7 Claims, 4 Drawing Figures

U.S. Patent  Aug. 6, 1985  Sheet 1 of 2  4,533,355
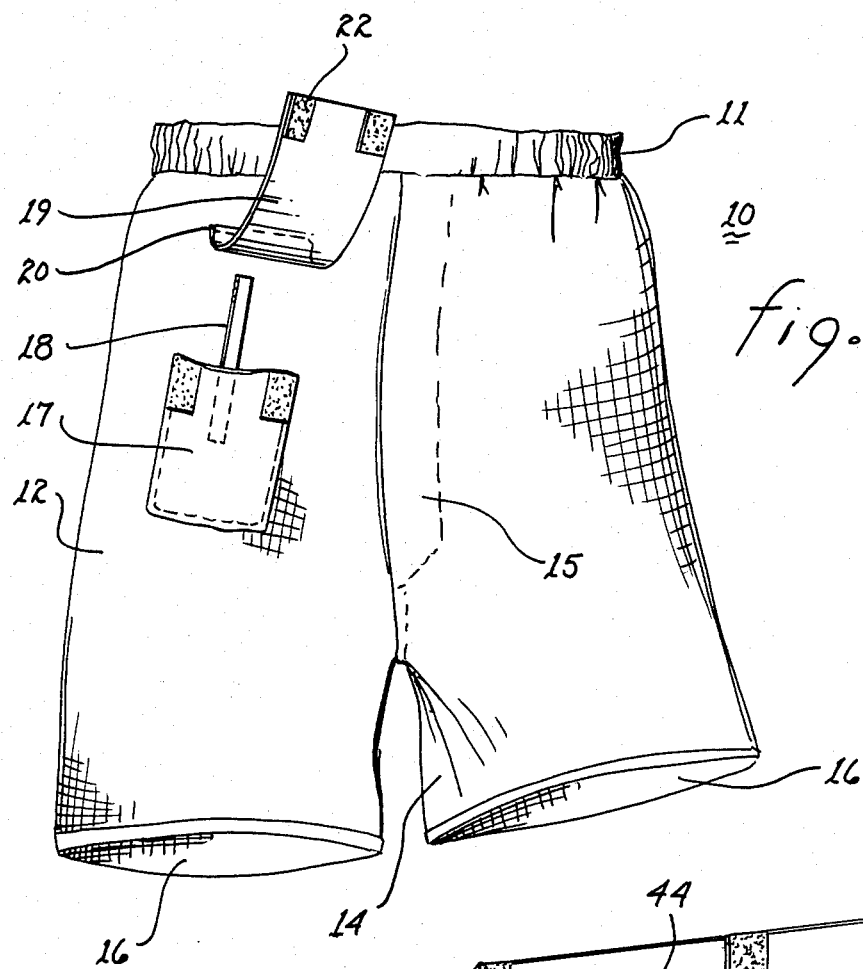
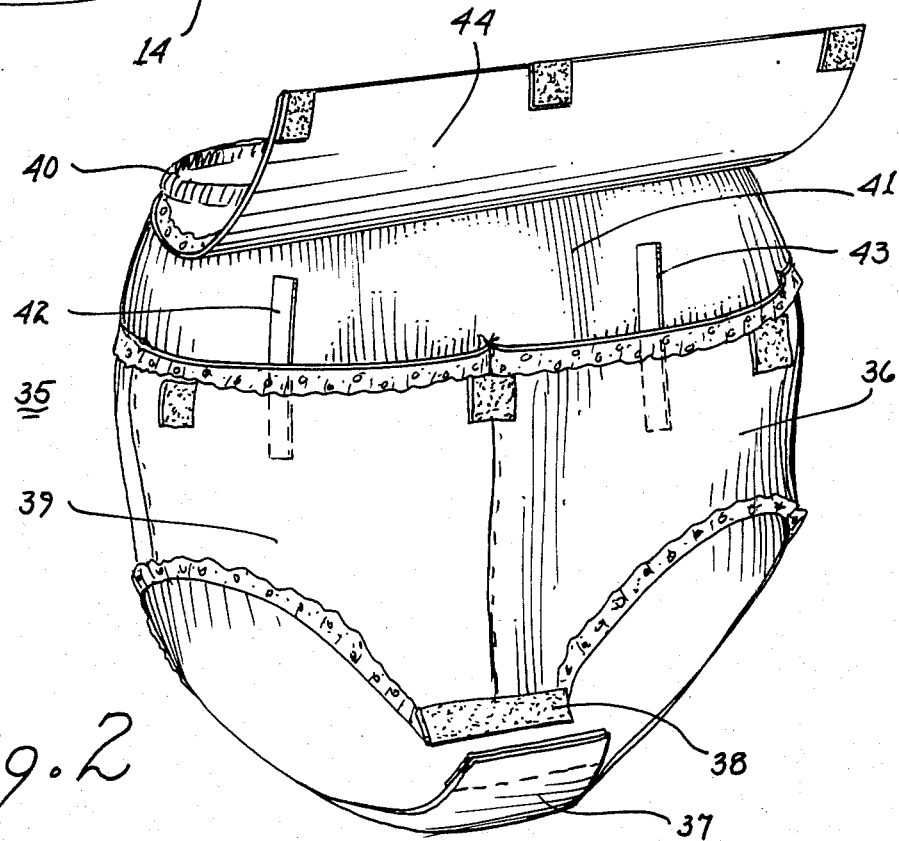

LOOSE-FITTING OSTOMY GARMENT

BACKGROUND OF THE INVENTION

This invention relates to novel garments for individuals required to utilize an ostomy appliance for the collection of body waste products.

An ostomy is a surgical operation that creates a new outside opening or stoma in the surface of an individual's body in order to compensate for the long term effects of the surgical procedure. Typically, the ostomy requires that a major portion of the large intestine be removed with the result that the individual is provided with the new opening to divert the waste products into a properly fitted appliance which is mechanically fitted to the body.

The increasing ability of medical science to diagnosis and successfully remove internal tumors has rapidly increased the number of individuals functioning in society today while wearing the ostomy appliance. A wide variety of appliances for the collection of waste products exiting the body through the stoma are presently commercially available. Two types of devices are well received: the first is comprised of a pouch with a combination sealing ring which fits about the stoma to provide a moisture barrier and an adhesive patch that adheres to a large area of skin surrounding the stoma. The second type utilizes a pouch, a sealing ring and a body encircling belt which maintains the sealing engagement of ring to skin by the pressure exerted against the body.

Heretofore, it has been recommended to an individual having undergone an ostomy to wear a support type garment over the portion of the torso containing the stoma in order to provide support for the organs in the proximate region of the body and also to insure that the appliance maintains its sealing engagement with the region around the stoma. The garment typically contains an aperture through which the waste collection pouch extends with perhaps an outside support device to prevent movement of the pouch. With the advent of improved moisture barriers and stronger adhesives along with different surgical techniques, the need for the body-girdling type of garment is not present for the majority of ostomy individuals.

In the case of an individual having experienced a colostomy, the stoma is placed within the region which encounters the waistband of conventional clothing. Consequently, the typical undergarments have not been capable of use by the individual wearing a fitted appliance. Further, the placement of an undergarment over the pouch of the appliance has the result that the pouch rests against the skin of the wearer. In active situations, the combination of the conventional waistband encircling the torso about the stoma plus the constant irritation of the skin adjacent the pouch has proved very uncomfortable to the wearer. One solution has been to wear two sets of undergarments with the first being located beneath the pouch and below the stoma while the second garment covers the entire region. This has been found unacceptable in most cases since the pouch is unsupported except if the individual is also provided with an encircling belt.

Consequently, the lack of appropriate styled and constructed undergarments has restricted the real and perceived ability of an individual having recently experienced an ostomy from again engaging in a normal active life. The individual is typically self-conscious about the fitted appliance and the inability to find comfortable clothing for an active life style often makes it difficult for prior activities to be resumed.

Accordingly, the present invention has as a primary objective the provision of a comfortable garment which protects the skin from irritation by the pouch and encircles the torso away from the stoma region. Furthermore the garment is constructed so that the appliance is not displayed for viewing by others in a dressing room or locker room environment. The garment is provided with a receiving portion for the free-end of the pouch which provides support but does not create significant back pressure to thereby decrease the effectiveness of the appliance. As a result, the present invention provides a garment which is comfortable, reduces irritation, provides support to reduce the chances of detachment in a manner which permits the garment to be worn during periods of normal activity, and shields the appliance from the view of others.

SUMMARY OF THE INVENTION

This invention relates to a loose-fitting garment for individuals having a surgical stoma and an ostomy appliance fitted in moisture-sealing relation to the skin of the individual in a region about the stoma.

The garment includes an encircling means for engaging the torso of the individual above the anatomical region containing the stoma and provides support for the garment as it is being worn. Extending downwardly from the encircling means is a shield means which loosely covers the lower torso of the wearer including the stoma region.

The shield means is provided with at least one receiving pocket on its exterior surface for receiving the free-end of the waste collecting appliance. The pocket is dimensioned to removably receive the lower portion of the pouch part of the appliance. An enlarged passageway is formed in the shield means adjacent the receiving pocket for accommodating the middle portion of the appliance sealingly connected to the stoma region.

Thus, the waist area of the wearer is kept free of a constricting encircling means and irritation of the stoma region is reduced. The appliance loosely extends through the passageway to the pocket which provides support for the free-end of the pouch as it fills over a period of time. The passageway is enlarged so that the torso of the individual can move within the garment without undue restriction.

Further, the garment prevents the individual's skin from encountering the surface of the pouch during normal activity so that irritation of the skin in this area below the stoma is essentially eliminated. By providing a cover affixed to the shield means above the receiving pocket, the cover can be utilized to screen the appliance from the view of others. The garment permits the addition of a crotch panel which can be made removable to aid the individual in carrying out the activities of normal life.

Further features and advantages of the invention will become more readily apparent from the following detailed description of specific embodiments of the invention when taken in conjunction with the accompanying drawings.

BRIEF DESCRIPTION OF THE DRAWINGS

FIG. 1 is a front view of one embodiment of the invention;

FIG. 2 is a front view of a second embodiment of the invention especially adapted for use by a female and able to accommodate both right and left stoma placement;

DESCRIPTION OF THE PREFERRED EMBODIMENTS

Figure 3:
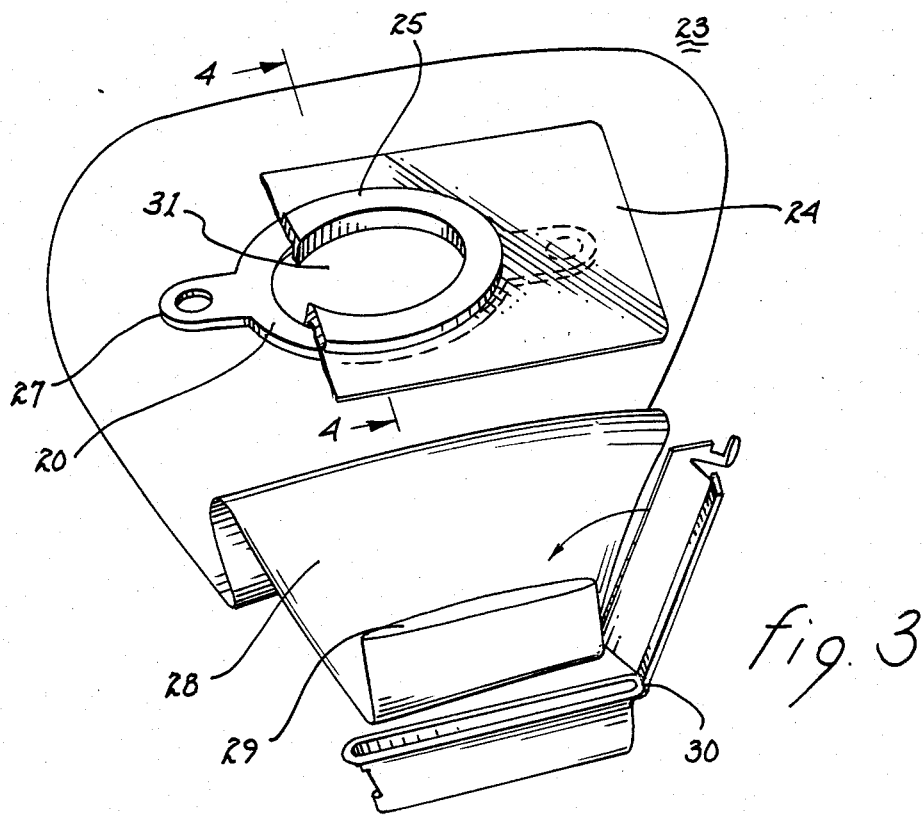
FIG. 3 is a perspective view of one type of ostomy appliance suitable for use with the present invention.

Referring now to FIG. 1, a garment 10 constructed in accordance with the present invention is shown comprising encircling means 11 adapted to frictionally engage the torso of the individual above the stoma region. The shield means 12 extends downwardly from the encircling means 11 to provide protection to the skin of the wearer and to shield this region of the body. A crotch piece 14 is provided beneath the fly front opening 15 in this embodiment. The vertical distance between the crotch bounded by leg openings 16 formed in the garment and the encircling means 11 is made larger than in the conventional garment to ensure that the encircling means engages the torso above the stoma region. Since the placement of the stoma on the body of the individual is determined in part by the nature of the colostomy or ileostomy operation performed, the distance between crotch piece and encircling means is made long enough to accommodate the average high placement corresponding to an entire or full descending colostomy.

Figure 4:
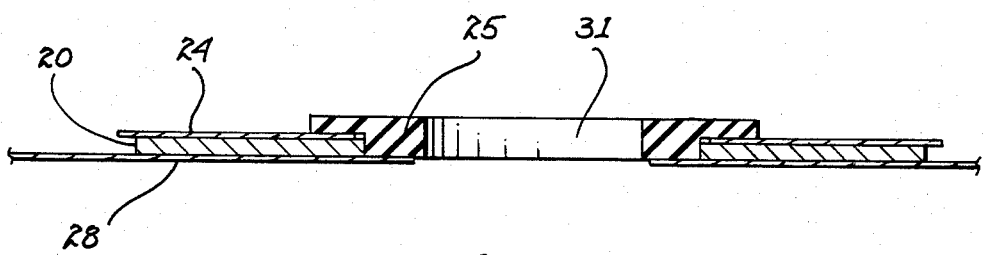
FIG. 4 is a side view in section taken along line 4—4 of the embodiment of FIG. 3.

A representative ostomy appliance 23 is shown in detail in FIGS. 3 and 4 wherein pouch 28 is terminated at its free end 29 by a removable locking device or clamp 30. The upper end of the pouch 28 contains an aperture 31 formed by flange member 27 and surrounded by a gasket 25. The gasket is formed of a deformable adhesive moisture-impervious material which forms a seal about the stoma. Underlying the gasket 25 is a large area adhesive sheet 24 which is affixed to the skin of the user to secure the appliance thereto and preserve the moisture barrier established by the gasket. The flange member 27 is normally bonded to the pouch 28 and provides the structural base 20 for the adhesive sheet 24 and gasket 25 as well as being adapted through the provision of connectors 27 to become part of a support belt worn by the individual. In the case of the active individual, the use of a belt may restrict the healing of the muscles subjected to the operation so that often the individual relies on the adhesive 24 for the support of the appliance. This is not always reliable especially in the case of activity in warm climates wherein moisture emanating from the skin tends to reduce the efficiency of the adhesive.

The assemblage of gasket 25, adhesive sheet 24, base 20 and pouch 28 is shown in the cross section of FIG. 4. The exposed surface of the deformable gasket 25 is placed in contact with the skin about the stoma. Then, the adhesive sheet 24 is pressed against the general region about the stoma to affix the appliance to the individual. The protection of the skin in the region surrounding the stoma is necessary to prevent blistering, roughening or pitting of the skin. The most common causes of skin disturbances result from a rupture of the seal thereby causing the skin around the stoma to become moist through contact with the discharge and from the chafing of the pouch 28 against the skin during active use. Since the appliance relies on the affixation to smooth undamaged skin, the presence of skin disturbances can restrict the activity of the wearer or require a different more cumbersome appliance to be used until healing has taken place.

When the appliance is affixed to the individual, the garment which is the subject of the present invention is donned with the encircling means 11 of the garment 10 shown in FIG. 1 being drawn to an area above the stoma. The pouch of the appliance is positioned to extend through the enlarged passageway 18 with the free end of the pouch placed in the pocket 17. At this time, the pouch is partially-filled or perhaps empty so that the passageway and the pocket exert no significant back-pressure on the pouch. This feature is important since any significant back pressure is likely to retard the filling of the pouch and thereby decrease the effectiveness of the appliance.

The passageway 18 extends both above and below the upper edge of the pocket 17 to insure that the individual has the ability to move within the garment without causing forces to be exerted on the pouch which tend to pull the appliance from the body of the individual. As the pouch fills during use, the pocket provides support without unduly limiting the relative movement of the individual within the garment.

A cover piece 19 is affixed to the exterior surface of the body shield portion 12 at seam 20 and is of sufficient length to extend down over the exposed upper portion of the passageway and the top portion of the pocket. Thus, the appliance is shielded from viewing by others and can be worn in dressing or locker rooms with confidence that others will not notice the appliance. The garment is provided with fastening means 22 on the corners of the cover 19 to insure that the appliance does not become available for others to view during normal activity. The garment of FIG. 1 is constructed for a right-hand placement of the stoma as shown by the position of the fly front 15. In practice, it may be desirable to provide a garment with multiple passageways and pockets so that the buyer need not specify right or left hand garments. While this embodiment is discussed primarily in terms of its use as an undergarment, it should be recognized that the design permits it to be made of durable fabric which can withstand wear for use as an outer garment, either as shorts or trousers of conventional length.

The embodiment of FIG. 2 is intended for use as a femine undergarment with adjacent receiving means located on the front of the garment to accommodate appliances affixed to either left or right hand positioned stomas.

This undergarment 35 is characterized by a relatively high rise or vertical distance between crotch piece and its associated fastening means 38 and the encircling means 40 which is intended to engage the body of the individual above the stoma region. A dual receiving means 39 formed with a central vertical seam is affixed to the front of the body shield 41 and is provided with spaced enlarged passageways 42 and 43 extending both above and below the upper edge of the dual receiving means. A cover piece 44 is attached to the shield means and is provided with removable fasteners at the center and at both edges. As shown, the conventional fabric fastener system is used although other fasteners may be employed if desired.

The undergarment 35 provides the shielding of the pouch of the appliance from direct contact with the skin of the individual. The combination of an enlarged passageway and a large receiving means for the free end of the pouch permit the wearer to engage in normal activities while still having the pouch in a supporting environment and not being subjected to forces which cause it to be pulled from contact with the skin of the individual. The garment is preferably feminized by the addition of accents as shown so that it is both attractive and provides the shielding of the appliance from the eyes of others when revealed in common dressing rooms and the like.

While the above description has referred to specific embodiments of the invention it is to be noted that variations and modifications may be made therein without departing from the scope of the invention as claimed.

I claim:

1. A loose-fitting garment for individuals having a surgical stoma and an ostomy appliance fitted thereover for the collection of waste material, said garment comprising:
    (a) encircling means for engaging the torso of the individual above the anatomical region containing the stoma and providing support for said garment;
    (b) shield means extending downwardly from the encircling means for loosely covering the lower torso including said stoma region;
    (c) at least one receiving means provided on the exterior of said shield means and positioned below said stoma region, said receiving means being dimensioned to removably receive the lower portion of an ostomy appliance therein; and
    (d) an enlarged passageway formed in said shield means adjacent said receiving means and through which an upper portion of the ostomy appliance extends.

2. The invention of claim 1 wherein said encircling means frictionally engages the torso above the waist of the individual.

3. The invention of claim 2 wherein said shield means is centrally joined to form a crotch panel for the individual.

4. The invention of claim 3 wherein said shield means is provided with a releasable central juncture forming said crotch panel.

5. The invention of claim 1 further comprising a cover piece affixed to said shield means above said passageway and extending downwardly so as to overlie a portion of the receiving means.

6. The invention of claim 1 further comprising a second receiving means spaced adjacent said at least one receiving means on the exterior of the shield means and a second enlarged passageway formed in the shield means adjacent the second receiving means.

7. The invention of claim 6 further comprising a cover piece affixed to the exterior of the shield means above the receiving means and extending downwardly so as to overlie a portion of the receiving means.

* * * * *